United States Patent [19]

Murdock

[11] 4,333,875

[45] Jun. 8, 1982

[54] 5,8-DIHYDROXY-1,4-BIS(-GUANIDINYLAMINO)ANTHRAQUINONES

[75] Inventor: Keith C. Murdock, Pearl River, N.Y.

[73] Assignee: American Cyanamid Company, Stamford, Conn.

[21] Appl. No.: 231,566

[22] Filed: Feb. 4, 1981

Related U.S. Application Data

[62] Division of Ser. No. 87,908, Oct. 24, 1979, Pat. No. 4,275,010.

[51] Int. Cl.³ .......................................... C07D 403/12
[52] U.S. Cl. ......................... 260/239 BC; 260/243.3; 260/245.6; 544/331; 548/336; 424/244; 424/250; 424/273 R

[58] Field of Search ........... 260/239 BC, 245.6, 243.3; 544/331; 548/336

[56] References Cited

U.S. PATENT DOCUMENTS 3,364,220 1/1968 Biel et al. ..................... 260/239 BC
4,275,010 6/1981 Murdock ............................. 260/380

*Primary Examiner*—Mary Lee
*Attorney, Agent, or Firm*—Edward A. Conroy, Jr.

[57] ABSTRACT

This disclosure describes 1,4-bis(guanidinylamino)-5,8-dihydroxyanthraquinones useful as chelating agents and for inhibiting the growth of transplanted mouse tumors.

8 Claims, No Drawings

5,8-DIHYDROXY-1,4-BIS(-GUANIDINYLAMINO)ANTHRAQUINONES

CROSS REFERENCE TO RELATED APPLICATION

This application is a division of my copending application Ser. No. 87,908, filed Oct. 24, 1979, now U.S. Pat. No. 4,275,010.

BRIEF SUMMARY OF THE INVENTION

This invention relates to new organic compounds and, more particularly, is concerned with novel 1,4-bis(-guanidinylamino)-5,8-dihydroxyanthraquinones which may be represented by the following general formula:

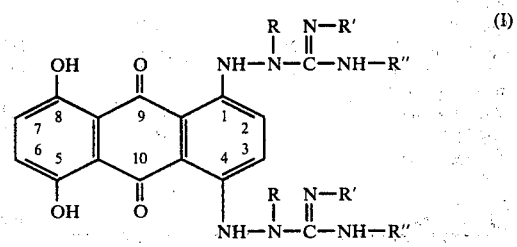

wherein R, R' and R" are selected from the group consisting of hydrogen and straight or branched chain lower alkyl ($C_1$-$C_4$) groups and R' and R" taken together is alkylene —$(CH_2)_n$—, where n is an integer from 2 to 4, inclusive.

Also included within the purview of the present invention are the leuco bases and tautomers thereof which may be represented by the following general formula:

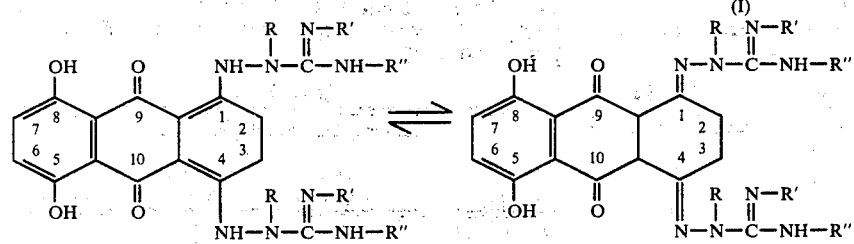

(II, Leuco Bases)     (III, Tautomeric Form)

wherein R, R', R" and n are as previously defined, and pharmaceutically acceptable acid-addition salts thereof.

DETAILED DESCRIPTION OF THE INVENTION

The novel compounds of the present invention are obtainable as reddish brown to blue crystalline materials having characteristic melting points and absorption spectra and which may be purified by leaching with lower alkanols since many of the free bases are insoluble in water and some of them are insoluble in most organic solvents. The organic bases of this invention (I, II, and III) form acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crsytalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

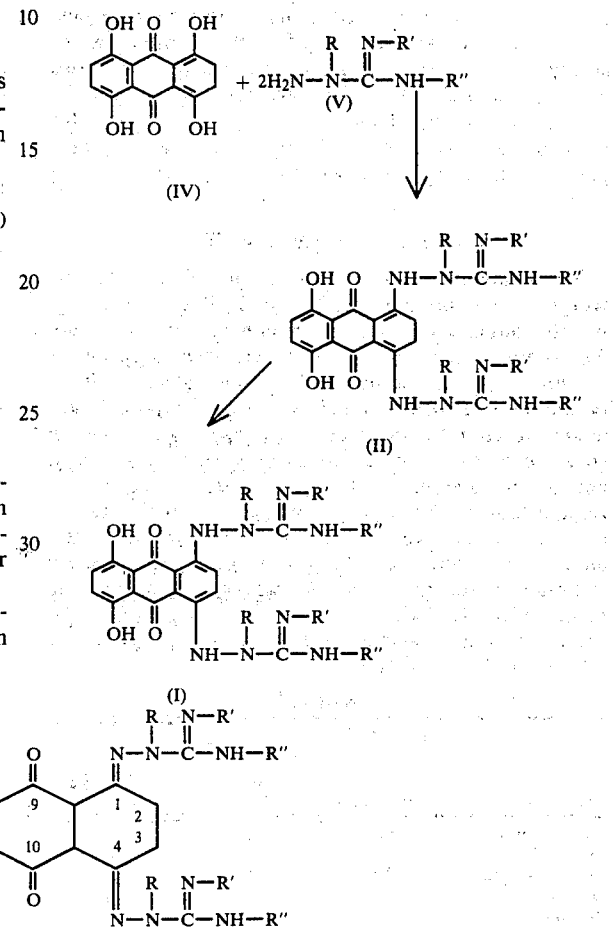

wherein R, R', R" and n are as hereinabove defined. In accordance with this reaction scheme, leuco 1,4,5,8-tetrahydroxyanthraquinone (IV) is condensed with an appropriate aminoguanidine (V) in a solvent such as N,N,N',N'-tetramethylethylenediamine, 2-methoxyethanol, methano, ethanol, water, dimethylformamide, or mixtures thereof at from about 40° C. to about 60° C. under an atmosphere of nitrogen for one or more hours to produce the corresponding leuco bases (II). The leuco bases (II) may be readily oxidized to the fully aromatic derivatives (I) by a variety of methods such as air oxidation or treatment with chloranil, hydrogen peroxide or sodium perborate.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inhibiting the growth of transplanted mouse tumors as established by the following tests.

Lymphocytic leukemia P388 test

The animals used are DBA/2 mice all of one sex, weighing a minimum of 17 g. and all within a 3 g. weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table I. The criterion for efficacy is $T/C \times 100 \geq 125\%$.

TABLE I

| Lymphocytic Leukemia P388 Test | | |
|---|---|---|
| Compound | Dose (mg./kg.) | Median Survival Time (Days) | T/C × 100 (Percent) |
| 1,1'-(5,8-Dihy- | 200 | 18.0 | 164 |
| droxy-1,4-anth- | 100 | 16.0 | 145 |
| raquinonylenedi- | 50 | 16.0 | 145 |
| imino)diguani- | 25 | 15.0 | 136 |
| dine dihydro- | 12 | 15.0 | 136 |
| chloride | | | |
| Control | | 11.0 | |
| 5-Fluorouracil | 60 | 21.5 | 195 |
| Leuco-5,8-dihy- | 200 | 23.0 | 209 |
| droxy-1,4-bis[2- | 100 | 19.0 | 173 |
| (2-imidazolin- | 50 | 18.0 | 164 |
| 2-yl)hydra- | 25 | 17.0 | 155 |
| zino]anthraquin- | 12 | 17.0 | 155 |
| one | | | |
| Control | | 11.0 | |
| 5-Fluorouracil | 60 | 20.5 | 186 |

Melanotic melanoma B16

The animals used are C57BC/6 mice, all of the same sex, weighing a minimum of 17 g. and all within a 3 g. weight range. There are normally 10 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with representative compounds of the present invention appear in Table II. The criterion for efficacy is $T/C \times 100 \geq 125\%$.

TABLE II

| Melanotic Melanoma B16 Test | | |
|---|---|---|
| Compound | Dose (Mg./kg.) | Median Survival Time (Days) | T/C × 100 (Percent) |
| 1,1'-(5,8-Dihy- | 100 | 33.0 | 220 |
| droxy-1,4-anth- | 50 | 32.0 | 213 |
| raquinonylenedi- | 25 | 29.0 | 193 |
| imino)diguani- | 12 | 23.5 | 158 |
| dine dihydro- | 6 | 22.0 | 147 |
| chloride | | | |
| Control | | 15.0 | |
| 5-Fluorouracil | 20 | 27.5 | 183 |
| Leuco-5,8-dihy- | 50 | 32.5 | 197 |
| droxy-1,4-bis [2- | 25 | 28.0 | 170 |
| (2-imidazolin- | 12 | 27.0 | 164 |
| 2-yl)hydra- | 6 | 26.5 | 161 |
| zino]anthraquin- | | | |
| one | | | |
| Control | | 16.5 | |
| 5-Fluorouracil | 20 | 16.5 | 100 |

Lymphocytic leukemia L1210 test

The procedure is the same as for the Lymphocytic leukemia P388 test except that the tumor transplant consists of lymphocytic leukemia L1210 inoculated at a concentration of $10^5$ cells/mouse with a mean survival time being calculated, and the test compound is administered only on day one. The results of this test with a representative compound of this invention appear in Table III below. The criterion for efficacy is $T/C \times 100 \geq 125\%$.

TABLE III

| Lymphocytic Leukemia L1210 Test | | |
|---|---|---|
| Compound | Dose (mg./kg.) | Median Survival Time (Days) | T/C × 100 (Percent) |
| 1,1'-(5,8-Dihy- | 200 | 12.8 | 165 |
| droxy-1,4-anth- | 100 | 10.8 | 139 |
| raquinonylenedi- | 50 | 10.8 | 139 |
| imino)diguani- | 25 | 10.3 | 132 |
| dine dihydro- | 12.5 | 10.0 | 128 |
| chloride | | | |
| Control | | 7.8 | |
| 5-Fluorouracil | 60 | 20.8 | 267 |

This invention will be described in greater detail in conjunction with the following specific Examples.

EXAMPLE 1

1,1'-(5,8-Dihydroxy-1,4-anthraquinonylenediimino)-diguanidine dihydrochloride

A mixture of 19.70 g. of aminoguanidine sulfate and 16.0 ml. of 10 N aqueous sodium hydroxide is stirred and triturated until all the lumps are gone. The mixture is diluted with 75 ml. of ethanol, chilled in an ice bath and dried for one hour with 90.0 g. of 3 A molecular sieves. The solids are removed by filtration and are washed sparingly with two 35 ml. portions of ethanol. The filtrate and washings are combined and de-aerated by bubbling nitrogen through for 15 minutes, then 10.97 g. of leuco-1,4,5,8,-tetrahydroxyanthraquinone is added under nitrogen. The mixture is stirred and heated under nitrogen in an oil bath at 50°–51° C. for one hour, then is allowed to cool for 16 hours. The mixture is chilled and the solid is collected by filtration and washed with cold ethanol to give 13.87 g. of a black solid which is the 2,3-dihydro derivative of the title product.

A stirred suspension of 11.60 g. of the 2,3-dihydro compound is oxidized by adding it to 7.50 g. of chloranil in 200 ml. of 2-methoxyethanol, then chilling with an ice bath during the dropwise addition of 15.0 ml. of 8 N hydrochloric acid in ethanol. The mixture is stirred for 16 hours at room temperature, then is thinned with diethyl ether. The solid is collected and washed with tetrahydrofuran to give 12.53 g. of a dark purple solid. A 10.0 g. portion of the purple solid is pulverized, stirred in 300 ml. of water at 23° C. for one hour, then centrifuged. The supernatant solution is decanted and filtered. The filtrate is freeze dried to yield 7.2 g. of the product of the Example as a red-brown solid.

EXAMPLE 2

Leuco-5,8-dihydroxy-1,4-bis[2-(imidazolin-2-yl)-hydrazino]anthraquinone

A solution of 3.94 g. of 2-hydrazino-2-imidazoline hydrochloride (U.S. Pat. No. 3,931,152) in 50 ml. of methanol is converted to the free base by passing it through a column containing 15 g. of a polystyrene quaternary ammonium hydroxide resin pre-washed with methanol. The sample is washed through the column with additional methanol. Evaporation of the eluate and washes gives 3.3 g. of a tan oil. A filtered solution of this oil in 40 ml. of N,N,N',N'-tetramethylethylenediamine:ethanol (1:1) is de-aerated by bubbling nitrogen through it for 15 minutes, then 2.02 g. of leuco-1,4,5,8-tetrahydroxyanthraquinone is added under nitrogen. The resulting mixture is stirred under nitrogen and heated in an oil bath at 50°–52° C. for one hour. The mixture is stored under nitrogen for 48 hours, the resulting solid is collected by filtration, washed once with N,N,N'N'-tetramethylethylenediamine and 3 times with ethanol to give 3.03 g. of the product of the Example as a red-brown solid.

EXAMPLE 3

Leuco-5,8-dihydroxy-1,4-bis[2-(2-imidazolin-2-yl)-2-methylhydrazino]anthraquinone A solution of 48.8 g. of 2-methylthio-2-imidazoline hydroiodide and 10.0 g. of methylhydrazine in 200 ml. of ethanol is heated at reflux for several hours, clarified and then cooled at −10° C. The precipitate is collected, washed with diethyl ether and dried, giving 2-(1-methylhydrazino)imidazoline hydroiodide.

This hydroiodide is converted to the free base and then allowed to react with one half of that molar amount of leuco-1,4,5,8-tetrahydroxyanthraquinone as in Example 2 to give the title compound as a dark solid.

EXAMPLE 4

Leuco-5,8-dihydroxy-1,4-bis[2-(4,5,6,7-tetrahydro-1H-1,3-diazepin-2-yl)hydrazino]anthraquinone A 6.41 g. amount of 2-hydrazino-4,5,6,7-tetrahydro-1H-1,3-diazepine hydroiodide (U.S. Pat. No. 3,931,152) is converted to the free base and allowed to react with 2.02 g. of leuco-1,4,5,8-tetrahydroxyanthraquinone as in Example 2, to give the title compound as a dark solid.

EXAMPLE 5

1,1'-(5,8-Dihydroxy-1,4-anthraquinonylenediimino)-3,3,3',3'-tetramethyldiguanidine dihydrochloride Basification of 9.2 g. of 1-amino-3,3-dimethylguanidine hydroiodide [Finnegan, et al., J. Org. Chem., 18, 779 (1953)] with 4.0 ml. of 10 N aqueous sodium hydroxide followed by reaction with 5.48 g. of leuco-1,4,5,8-tetrahydroxyanthraquinone and oxidation with chloranil as in Example 1 gives the desired product as a dark solid.

EXAMPLE 6

1,1'-(5,8-Dihydroxy-1,4-anthraquinonylenediimino)-3,3'-dimethyldiguanidine dihydrochloride Processing of 1-amino-3-methylguanidine hydroiodide as in Example 1 gives the title compound.

EXAMPLE 7

1,1'-(5,8-Dihydroxy-1,4-anthraquinonylenediimino)-3,3'-di(1-butyl)diguanidine dihydrochloride The title compound is obtained from 1-amino-3-(1-butyl)guanidine hydroiodide [Short, et. al., J. Med. Chem., 6, 275 (1963)] by the procedure of Example 1.

We claim:

1. A compound selected from the group consisting of those of the formula:

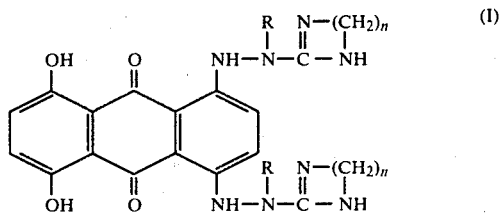

wherein R is selected from the group consisting of hydrogen and straight or branched chain lower alkyl ($C_1$–$C_4$) groups and n is an integer from 2 to 4, inclusive.

2. A compound selected from the group consisting of those of the formula:

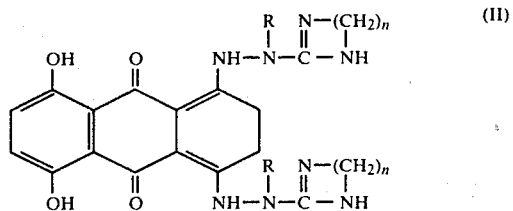

wherein R is selected from the group consisting of hydrogen and straight or branched chain lower alkyl ($C_1$–$C_4$) groups and n is an integer from 2 to 4, inclusive.

3. The compound according to claim 2, leuco-5,8-dihydroxy-1,4-bis[2-(2-imidazolin-2-yl)hydrazino]anthraquinone.

4. The compound according to claim 2, leuco-5,8-dihydroxy-1,4-bis[2-(2-imidazolin-2-yl)-2-methylhydrazino]anthraquinone.

5. The compound according to claim 2, leuco-5,8-dihydroxy-1,4-bis[2-(4,5,6,7-tetrahydro-1H-1,3-diazepin-2-yl)hydrazino]anthraquinone.

6. The compound according to claim 1, 5,8-dihydroxy-1,4-bis[2-(2-imidazolin-2-yl)hydrazino]anthraquinone.

7. The compound according to claim 1, 5,8-dihydroxy-1,4-bis[2-(2-imidazolin-2-yl)-2-methylhydrazino]anthraquinone.

8. The compound according to claim 1, 5,8-dihydroxy-1,4-bis[2-(4,5,6,7-tetrahydro-1H-1,3-diazepin-2-yl)hydrazino]anthraquinone.

* * * * *